(12) United States Patent
Lin

(10) Patent No.: US 6,392,196 B1
(45) Date of Patent: May 21, 2002

(54) THERMAL EARMUFF

(76) Inventor: Ku-Shen Lin, PO Box 82-144, Taipei (TW)

( * ) Notice: Subject to any disclaimer, the term of this patent is extended or adjusted under 35 U.S.C. 154(b) by 0 days.

(21) Appl. No.: 09/875,867

(22) Filed: Jun. 8, 2001

(51) Int. Cl.⁷ .............................................. H01M 10/50
(52) U.S. Cl. ...................... 219/211; 219/528; 219/535; 219/209; 2/209; 2/905
(58) Field of Search ................................ 219/211, 209, 219/528, 535, 549; 2/209, 905

(56) References Cited

U.S. PATENT DOCUMENTS

| | | | | |
|---|---|---|---|---|
| 4,546,215 A | * | 10/1985 | Ferraro | 179/156 R |
| 4,669,129 A | * | 6/1987 | Chance | 2/209 |
| 4,674,199 A | * | 6/1987 | Lakic | 36/2 |
| 5,395,400 A | * | 3/1995 | Stafford et al. | 607/109 |
| 5,486,680 A | * | 1/1996 | Lieberman | 219/211 |

\* cited by examiner

Primary Examiner—Teresa Walberg
Assistant Examiner—Shawntina T. Fuqua
(74) Attorney, Agent, or Firm—A & J

(57) ABSTRACT

A thermal earmuff includes an inner cover having a circular partition formed with a first circular recess at one side thereof and a second circular recess at another side thereof, a circular member having two opposite circumferential edges provided with two curved shoulders and force-fitted within the second recess of the circular partition to support the inner cover, an outer side of the circular member being provided with a clamping device, a heating member secured on an outer side of the circular member and provided with a heating filament facing the through holes of the circular partition, an outer cover enclosing the inner cover, a head band having a plurality of teeth at two ends each of which is inserted into the slot with the teeth of the head band engaged with the teeth of the clip, and power supplying means electrically connected with the filament

3 Claims, 4 Drawing Sheets

THERMAL EARMUFF

BACKGROUND OF THE INVENTION

1. Field of the Invention

This invention is related to a thermal earmuff and in particular to one which can warm up a user's ears in a short time.

2. Description of the Prior Art

The need for persons to don protective clothing during times of exposure to cold temperatures has always been known. Indeed, various garments have been specially developed to protect different parts of the body; among these are various hats, caps and other headgear adapted to protect a wearer's ears. For example, some hats and caps include flap portions that can be either extended downwardly over the ears when worn on the head or retracted away from the ears, if desired. Stocking-type caps are often sized so that they may be rolled into a thick peripheral margin away from the ears but unrolled over the ears when extra ear protection is sought. Some stocking-type caps are constructed to encase the entire head, including the ears, leaving only small openings for the eyes, nose and mouth.

In addition to these examples of headwear, specifically designed independent protectors for the ears, are known and are commonly referred to as earmuffs, and it is to this type of ear protector that the present invention is concerned. Typically, earmuffs comprise a pair of earmuff elements each in the form of a large, thick, insulated disk sized to cover the ear. These earmuff elements are rather stiff constructs, and they are usually interconnected by an arcuate strip of metal or plastic that is stiff, yet resilient enough so that the earmuff elements may be positioned over the ears or held in position with the spring-like action of the band member which arches over and is supported by the top of the wearer's head. However, such earmuffs cannot warm up a user's ears in a short time.

Therefore, it is an object of the present invention to provide a thermal earmuff which can obviate and mitigate the above-mentioned drawbacks.

SUMMARY OF THE INVENTION

This invention is related to a thermal earmuff.

It is the primary object of the present invention to provide a thermal earmuff which can warm up a user's ears in a short time.

It is another object of the present invention to provide a thermal earmuff which will warm up a user's ears in a indirect manner.

It is still another object of the present invention to provide a thermal earmuff which can be affixed to a hat as desired.

It is a further object of the present invention to provide a thermal earmuff which is simple in construction and fit for practical use.

According to a preferred embodiment of the present invention, a thermal earmuff comprising: an inner cover made of flexible material and having a circular partition formed with a first circular recess at one side thereof and a second circular recess at another side thereof, said circular partition formed with a plurality of through holes connecting said first circular recess with said second circular recess, a circular member having two opposite circumferential edges provided with two curved shoulders and force-fitted within said second recess of said circular partition to support said inner cover, an outer side of said circular member being provided with a clamping device which includes a seat mounted within said first circular recess of said circular member, a clip pivotally connected with said seat, and a spring mounted on said seat and having an arm which forces an end of said clip against said outer cover, said clip being provided with a plurality of teeth at an upper portion and a slot at a lower portion, a heating member secured on an outer side of said circular member and provided with a heating filament facing said through holes of said circular partition enabling causing heat produced by said heating filament to pass through said holes to said first circular recess when electrical current flows through said heating filament, said heating member being provided with an electrical socket electrically connected with said heating filament, an outer cover enclosing said inner cover, a head band having a plurality of teeth at two ends each of which is inserted into said slot with said teeth of said head band engaged with said teeth of said clip, and power supplying means electrically connected with said filament.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENT

Figures 1, 5:
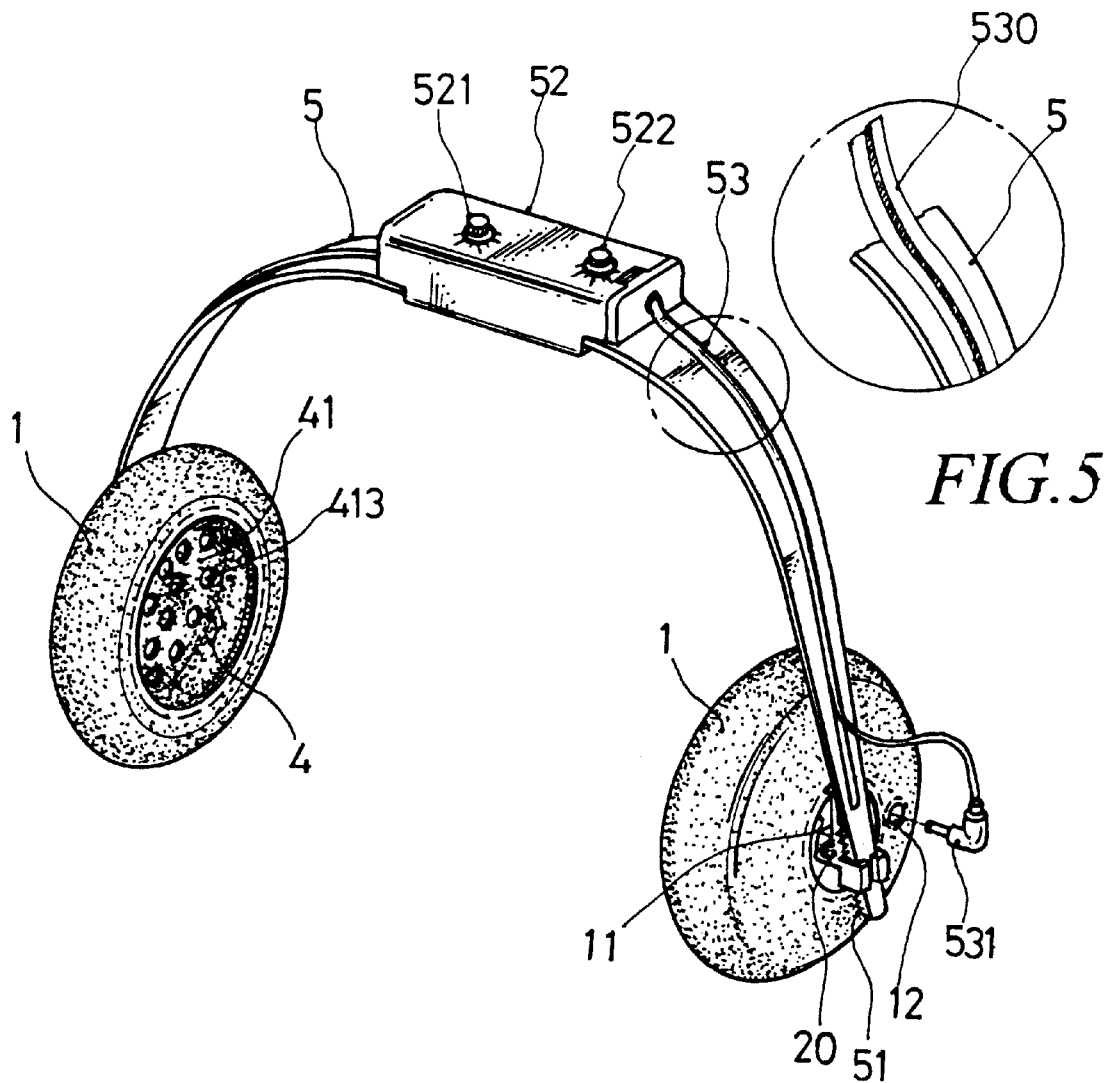
FIG. 1 is a perspective view of the present invention.
FIG. 5 illustrates the replacement of the circular electrical cord with a flat-type electrical cord.

For the purpose of promoting an understanding of the principles of the invention, reference will now be made to the embodiment illustrated in the drawings. Specific language will be used to describe same. It will, nevertheless, be understood that no limitation of the scope of the invention is thereby intended, alterations and further modifications in the illustrated device, and further applications of the principles of the invention as illustrated herein being contemplated as would normally occur to one skilled in the art to which the invention relates.

Referring to the drawings and in particular to FIGS. 1, 2, 3 and 4 thereof, the thermal earmuff according to the present invention generally comprises an outer cover 1, a circular member 2, a heating member 3, an inner cover 4 and a head band 5.

The inner cover 4 is made of flexible material and includes a circular partition 41 formed with a first circular recess 411 at one side and a second circular recess 412 at the other side. The circular partition 41 is formed with a plurality of through holes 413 so that the first circular recess 411 is in communication with the second circular recess 412. The first circular recess 411 is configured to receive an ear (not shown) of a user.

Figure 2:
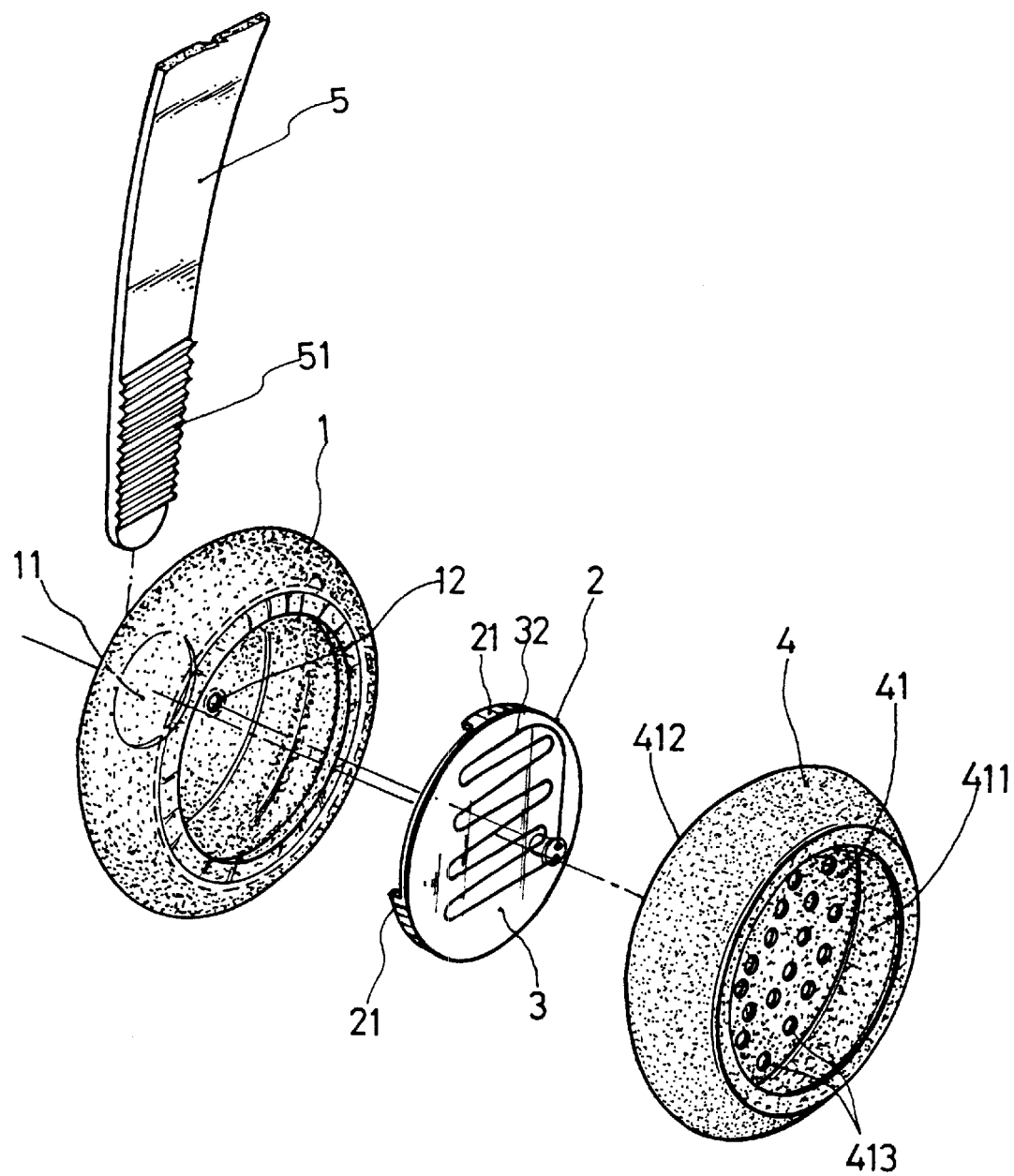
FIG. 2 is an exploded view of the present invention.
Figure 3:
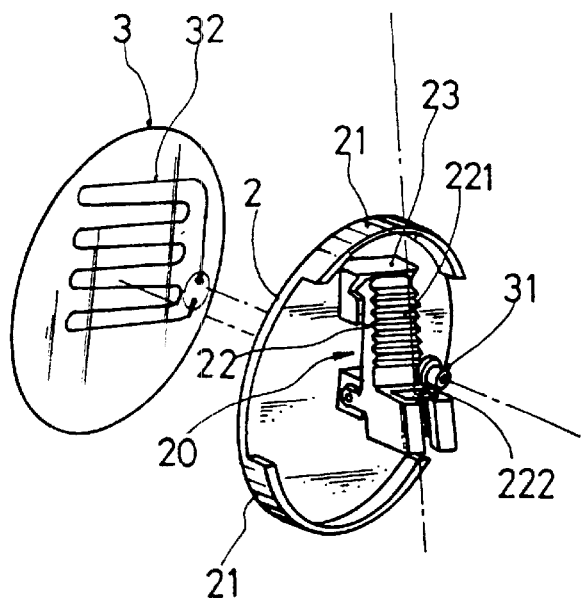
FIG. 3 illustrates the relationship between the circular member and the heating member.

As shown in FIGS. 2 and 3, the circular member 2 is formed with two curved shoulders 21 at two opposite circumferential edges and force-fitted within the second recess 412 of the circular partition 41 so that the curved shoulders 21 will support the shape of the inner cover 4. The heating member 3 is adhered or otherwise secured on an outer side of the circular member 2 and provided with a heating filament 31 facing the through holes 413 of the circular partition 41, so that the heat produced by the heating filament 31 will pass through the holes 412 to the first circular recess 411 when electrical current flows through the heating filament 31, thereby warming the ear of the user. The heating member 2 is provided with an electrical socket 32 electrically connected with the heating filament 31.

Figure 4:
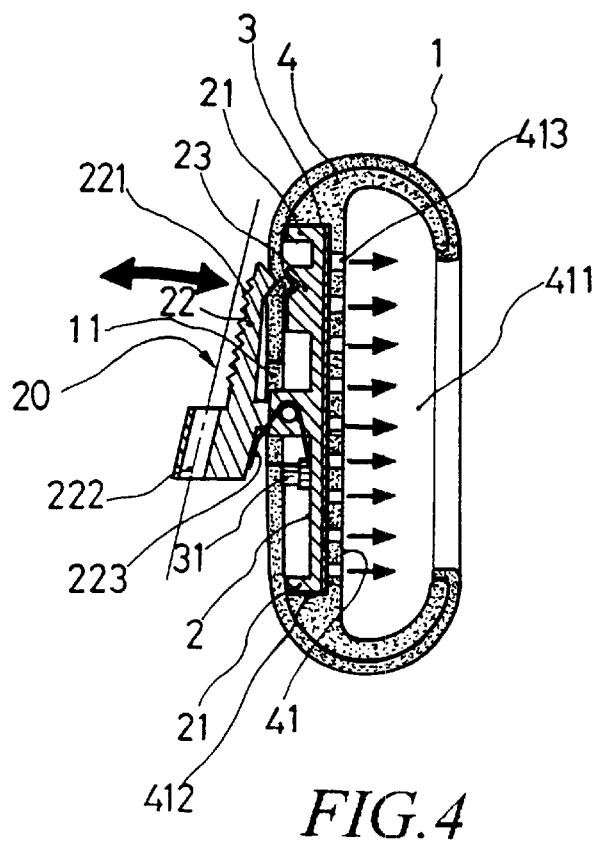
FIG. 4 is a sectional view of the present invention.

Referring to FIG. 4, the other side of the circular member 2 is provided with a clamping device 20 which includes a seat 23 mounted within the first circular recess 412 of the circular member 41, and a clip 20 pivotally connected with the seat 23. The outer cover 1 is arranged on the inner cover 4. A spring 223 is mounted on the seat 23 and has an arm which forces an end of the clip 20 against the outer cover 1. The clip 20 is provided with a plurality of teeth 221 at the upper portion and a slot 222 at the lower portion.

The head band 5 has a plurality of teeth 51 at two ends each of which is inserted into the corresponding slot 222 with the teeth 51 of the head band 5 engaged with the teeth 221 of the clip 20, so that the present invention can be adjusted in length to meet a user's need. The top of the head band 5 is provided with a control box 52 which has a power switch 521 and a temperature control button 522 which are electrically connected with the heating filaments 31 via a circular electrical cord 53. The circular electrical cord 53 has an electrical plug 531 adapted to engage with the electrical socket 31 of the circular member 3. The circular electrical cord 53 may be replaced m with a flat-type electrical cord 530 (see FIG. 5).

Figure 6:
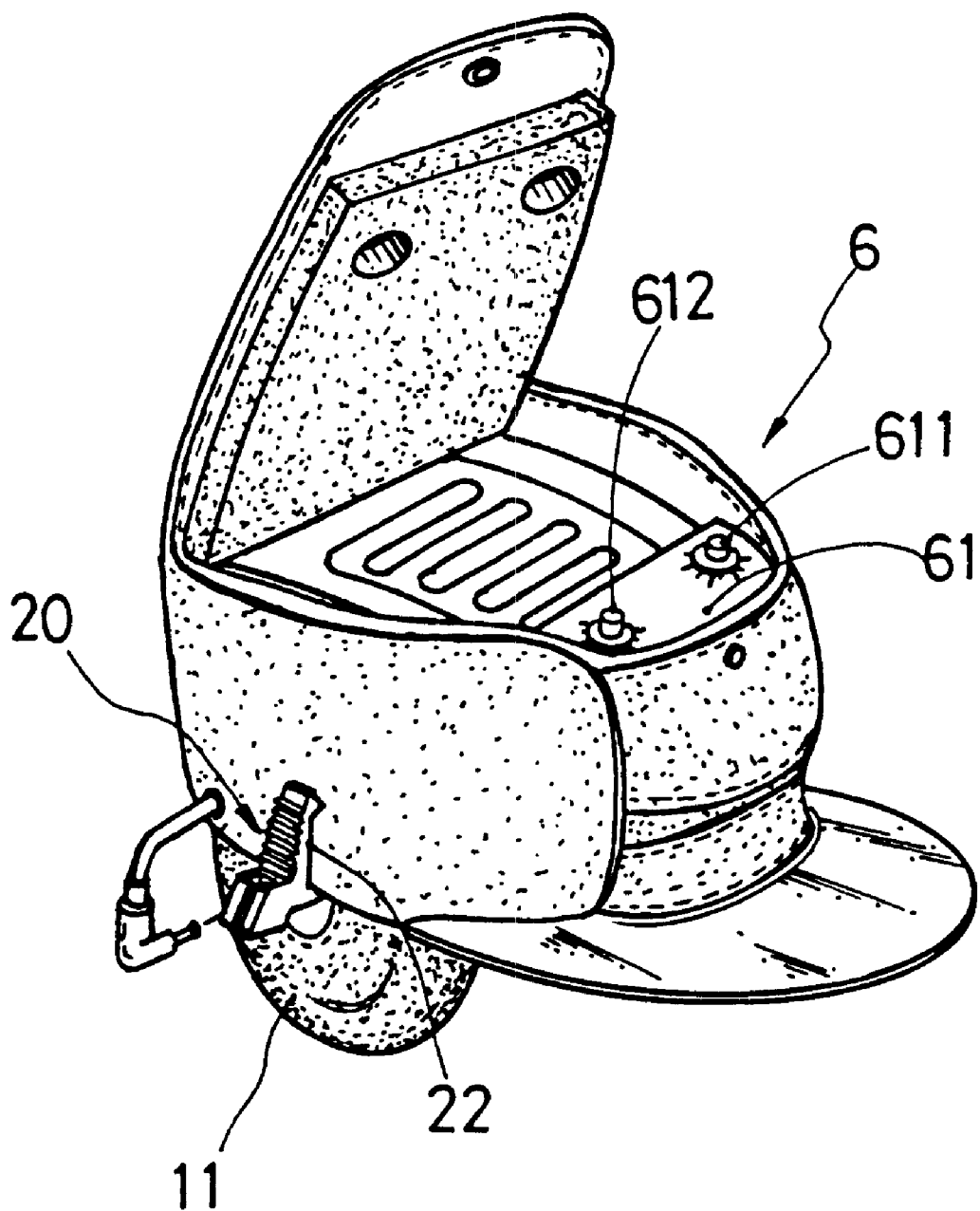
FIG. 6 illustrates another preferred embodiment of the present invention.

FIG. 6 illustrates a second preferred embodiment of the present invention. As shown, the outer cover 1 is mounted on each side of a hat 6 by the clamp 20 and the hat 6 is provided at the top with a control box 61 having a power switch 611 and a temperature control button 612 for controlling the heat supplied to the hat 6.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from tile spirit of the present invention.

I claim:

1. A thermal earmuff comprising:

an inner cover made of flexible material and having a circular partition formed with a first circular recess at one side thereof and a second circular recess at another side thereof, said circular partition formed with a plurality of through holes connecting said first circular recess with said second circular recess;

a circular member having two opposite circumferential edges provided with two curved shoulders and force-fitted within said second recess of said circular partition to support said inner cover, an outer side of said circular member being provided with a clamping device which includes a seat mounted within said first circular recess of said circular member, a clip pivotally connected with said seat, and a spring mounted on said seat and having an aim which forces an end of said clip against said outer cover, said clip being provided with a plurality of teeth at an upper portion and a slot at a lower portion;

a heating member secured on an outer side of said circular member and provided with a heating filament facing said through holes of said circular partition enabling causing heat produced by said heating filament to pass through said holes to said first circular recess when electrical current flows through said heating filament, said heating member being provided with an electrical socket electrically connected with said heating filament;

an outer cover enclosing said inner cover;

a head band having a plurality of teeth at two ends each of which is inserted into said slot with said teeth of said head band engaged with said teeth of said clip; and power supplying means electrically connected with said filament.

2. The thermal earmuff as claimed in claim 1, wherein said heating member is provided with an electrical socket.

3. The thermal earmuff as claimed in claim 1, wherein said power supplying means has an electrical cord provided with an electrical plug engageable with said electrical socket.

* * * * *